United States Patent [19]

Clemence et al.

[11] Patent Number: 5,348,971

[45] Date of Patent: * Sep. 20, 1994

[54] INDANES USEFUL AS ANALGESICS

[75] Inventors: Francois Clemence; Michel Fortin, both of Paris; Gilles Hamon, Le Raincy; Odile Le Martret; Anne-Marie Moura, both of Paris, all of France

[73] Assignee: Roussel Uclaf, France

[*] Notice: The portion of the term of this patent subsequent to Aug. 10, 2010 has been disclaimed.

[21] Appl. No.: 105,329

[22] Filed: Aug. 9, 1993

Related U.S. Application Data

[63] Continuation of Ser. No. 954,332, Sep. 30, 1992, abandoned, which is a continuation of Ser. No. 450,630, Dec. 14, 1989, abandoned.

[30] Foreign Application Priority Data

Dec. 16, 1988 [FR] France .................. 88 10605

[51] Int. Cl.$^5$ .................. A61K 31/40; C07D 295/073
[52] U.S. Cl. ..................... 514/428; 548/568
[58] Field of Search ................ 514/428; 548/568

[56] References Cited

U.S. PATENT DOCUMENTS 4,876,269 10/1989 Pennev et al. .................. 514/429

Primary Examiner—Patricia L. Morris
Assistant Examiner—Jacqueline Haley
Attorney, Agent, or Firm—Bierman and Muserlian

[57] ABSTRACT

Novel indanes in all possible stereoisomer forms of the formula

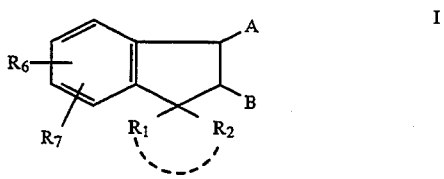

wherein the substrates are as defined in the application and their non-toxic, pharmaceutically acceptable acid addition salts and their hydrates are disclosed as having central analgesic properties as well as antiarrhythmic and diuretic activities.

3 Claims, No Drawings

INDANES USEFUL AS ANALGESICS

PRIOR APPLICATIONS

This application is a continuation of U.S. patent application Ser. No. 954,332, filed Sep. 30, 1992 which is a continuation of U.S. patent application Ser. No. 450,630 filed Dec. 14, 1989, both now abandoned.

STATE OF THE ART

EPO Application No. 87-401734.6 published under No. 0,258,096 describes indanes in possible stereoisomer forms of the formula

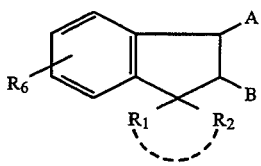

wherein $R_6$ is hydrogen or halogen or alkyl or alkoxy of 1 to 5 carbon atoms, $R_1$ and $R_2$ are individually hydrogen or alkyl of 1 to 5 carbon atoms or taken together with the carbon atom to which they are attached form cycloalkyl of 3 to 6 carbon atoms and optionally contain a sulfur, oxygen or nitrogen atom in the ring, one of A and B is

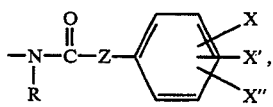

R is hydrogen or alkyl of 1 to 5 carbon atoms, Z is linear —$(CH_2)_n$—, n is 0 to 5 or —$CH_2O$— or branched alkylene of 2 to 8 carbon atoms, X, X' and X" are individually selected from the group consisting of hydrogen, alkyl and alkoxy of 1 to 4 carbon atoms, halogen, —OH, —$CF_3$, —$NO_2$, —$NH_2$, mono- and dialkylamino and sulfoamino and the other of A and B is

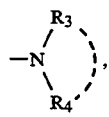

$R_3$ and $R_4$ are individually hydrogen or alkyl of 1 to 5 carbon atoms or taken together with the nitrogen atom forming a 5 to 6 member heterocycle optionally containing a sulfur or oxygen or nitrogen optionally substituted with alkyl of 1 to 4 carbon atoms and its non-toxic, pharmaceutically acceptable acid addition salts.

Example 9 of the said application describes [trans (+)] N-(2,3-dihydro-2-(1-pyrrolidinyl)-1H-inden-1-yl]-N-methyl-3-nitro-benzene-acetamide and its hydrochloride of the formula

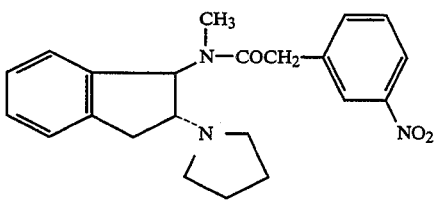

The said compound is obtained starting with [trans (+)] 2,3-dihydro-N-methyl-2-(1-pyrrolidinyl)-1H-inden-1-amine described in Step A of Example 1 of the application. The separation of the latter into its A and B isomers is described in Step A of Example 16 of the application.

Additional related art includes U.S. Pat. Nos. 4,360,531; 4,359,476; 4,466,977 and 4,460,600 and European applications No. 0,260,555 and No. 0,005,821.

OBJECTS OF THE INVENTION

It is an object of the invention to provide the novel compounds of formula I and their non-toxic, pharmaceutical acceptable acid addition salts and a process for their preparation.

It is another object of the invention to provide novel analgesic compositions and a novel method of relieving pain in warm-blooded animals.

These and other objects and advantages of the invention will become obvious from the following detailed description.

THE INVENTION

The novel compounds of the invention are selected from the group consisting of indanes in all possible stereoisomer forms of the formula

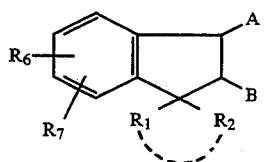

wherein $R_1$ and $R_2$ are individually selected from the group consisting of hydrogen and alkyl of 1 to 6 carbon atoms or taken together with the carbon atoms to which they are attached form a cycloalkyl of 3 to 6 carbon atoms and may contain a heteroatom in the ring selected from the group consisting of —S—, —O— and —N—, when $R_6$ and $R_7$ are individually selected from the group consisting of halogen and alkyl and alkoxy of 1 to 5 carbon atoms, one of A and B is

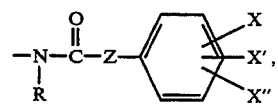

R is hydrogen or alkyl of 1 to 5 carbon atoms, Z is —$CH_2O$— or linear alkylene —$(CH_2)_n$—, n is 0 to 5 or branched alkylene of 2 to 8 carbon atoms, X, X' and X" are individually selected from the group consisting of hydrogen, alkyl and alkoxy of 1 to 4 carbon atoms, halogen, —OH, —$CF_3$, —$NO_2$, —$NH_2$, mono- and dialkylamino and sulfoamino and the other of A and B is

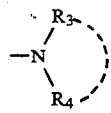

R3 and R4 are individually selected from the group consisting of hydrogen and alkyl of 1 to 5 carbon atoms or taken together with the nitrogen atom form a 5 to 6 member ring heterocycle optionally containing heteroatom selected from the group consisting of a nitrogen oxygen or sulfur or nitrogen atom optionally substituted with alkyl of 1 to 4 carbon atoms, when $R_6$ and $R_7$ are hydrogen, B is pyrrolidine and A is N-methyl-3-nitro-benzene-acetamide or 3,5-bis-(1,1-dimethyl-ethyl)-4-hydroxy-N-methyl-benzamide or 3,4-dichloro-N-methyl-benzene-acetamide or A is 3,4-dichloro-N-methyl benzene-acetamide and B is methyl-(2-phenethyl)-amino or (2-furylmethyl)-methylamino or 4-(2-methoxy-phenyl)-1-piperazinyl and when one of $R_6$ and $R_7$ is hydrogen and the other is chlorine, B is pyrrolidine and A is N-methyl-3-nitro-benzene-acetamide and their non-toxic, pharmaceutically acceptable acid addition salts.

Examples of suitable acids to form the non-toxic, pharmaceutically acceptable acid addition salts are inorganic acids such as nitric acid, hydrochloric acid, hydrobromic acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkanesulfonic acids such as methanesulfonic acid and arylsulfonic acids such as benzene sulfonic acid.

The compounds of formula I and their salts may be in the anhydrous or hydrated form such as anhydrous hydrochloride salt or the hydrated hydrochloride salt.

Among the preferred compounds of formula I are those wherein A and B have the trans configuration, those wherein

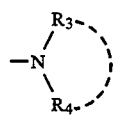

is pyrrolidine, those wherein $R_1$ and $R_2$ are both hydrogen and those wherein

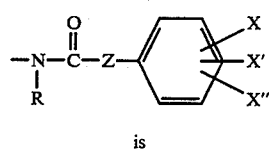

is

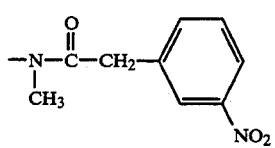

and their hydrates and their acid addition salts. Particularly preferred are those wherein $R_6$ and $R_7$ are individually hydrogen or chlorine and their hydrates and acid addition salts.

Among the specific compounds of the invention are (1S,2S) N-[2,3-dihydro-2-(1-pyrrolidinyl)-1H-inden-1-yl]-N-methyl-3-nitro benzene-acetamide and its hydrochloride and trans (+) N-[5-chloro-2,3-dihydro-2-(1-pyrrolidinyl)-1H-inden-1-yl]-N-methyl-3-nitro-benzene-acetamide and its hydrochloride.

The process of the invention for the preparation of the products of formula I in which A and B have the trans configuration comprises reacting a compound of the formula

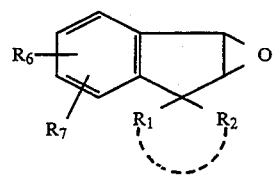

wherein $R_1$, $R_2$, $R_6$ and $R_7$ have the above definitions with an amine of the formula

wherein R has the above definition and $R_5$ is an amine protective group preferably benzyl, to obtain a compound of the formula

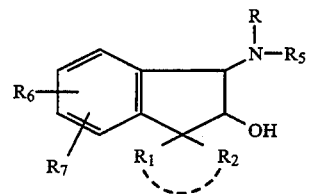

reacting the latter with an hydroxyl activator and reacting the latter with an amine of the formula

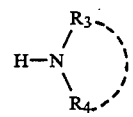

wherein $R_3$ and $R_4$ have the above definitions to obtain a compound of the formula

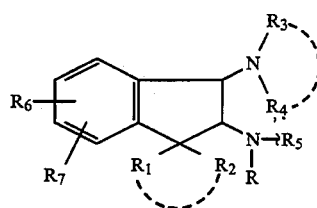

removing the amine protective group to form a compound of the formula

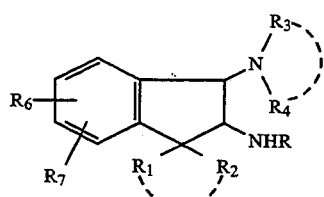  VII

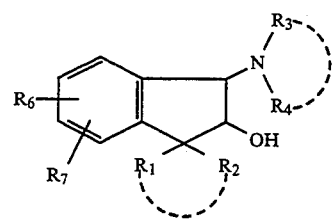  IX treating the latter with an acid or a functional derivative thereof of the formula

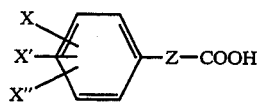  VIII wherein Z, X, X' and X" have the above definitions to obtain a compound of formula I wherein A is

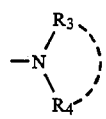

and B is

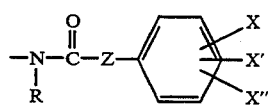

or with an amine of the formula

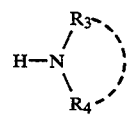

to obtain a compound of the formula reacting the latter with an amine of the formula $NH_2$-R X wherein R has the above definition after activating the hydroxyl to obtain a compound of the formula

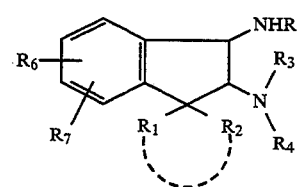  XI and reacting the latter with an acid of formula VIII or a functional derivative thereof to obtain a compound of formula I wherein A is $$-\overset{\overset{O}{\|}}{\underset{R}{N}}-C-Z-\text{Ar}(X,X',X'') \quad \text{and B is} \quad -N(R_3)(R_4)$$

which may be resolved into their optical isomers and which may be reacted with an acid to form the acid addition salt.

In a preferred mode of the process of the invention, methane sulfonyl chloride is used to activate the hydroxyl of the compounds of formulae IV and IX and the protective group of the compound of formula VI is benzyl which is removed by catalytic hydrogenation, preferably with a palladium catalyst. The activation of the hydroxy of the compounds of formula VII or XI in the presence of carbonyldiimidazole or activated with mixed acids. The resolution may be effected by the usual methods.

The compounds of formula I with A and B having the cis configuration may be prepared by the following reaction scheme

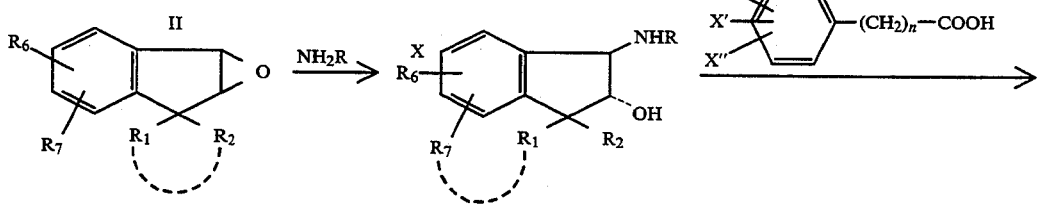

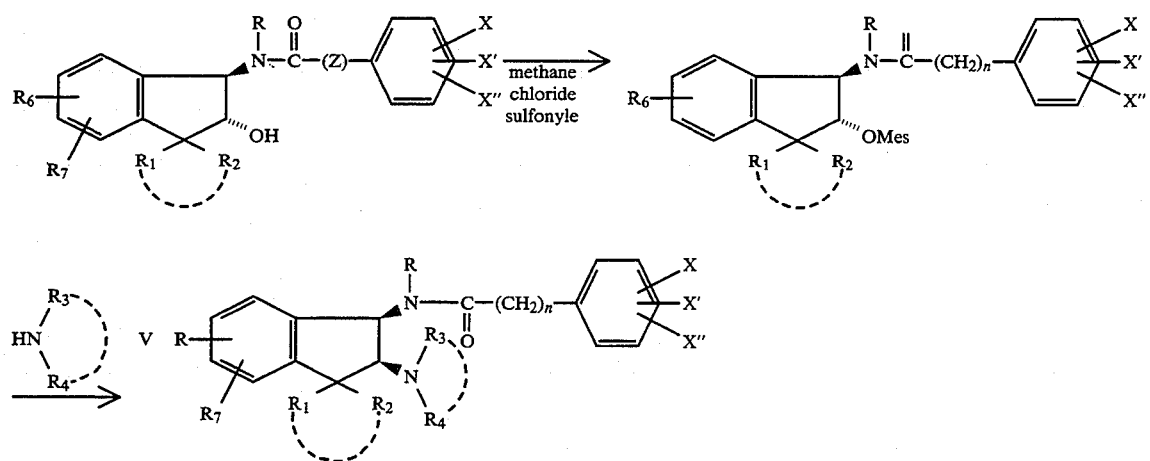

The novel analgesic compositions of the invention are comprised of an analgesically effective amount of at least one compound of formula I, its non-toxic, pharmaceutically acceptable acid addition salts and its hydrates and an inert pharmaceutical carrier. The compositions may be in the form of tablets, dragees, gelules, capsules, granules, suppositories, pomades, creams, gels, injectable solutions or suspensions and aerosols preparations.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and preservatives.

In addition to analgesic activity, the compositions have a strong affinity for opiate receptors, especially K receptors and antiarrythmic and diuretic activities.

The compositions are useful for the treatment of cerebral ischemia, treatment of pain of any origin such as muscular, articular or nervous pain, dental pain, migraines, zona in the treatment of intense pain, particularly rebellious agent antalgics in the treatment of pancreatitis, nephretic or biliary colics and treatment of post-operative and post-traumatic pains. The compositions are useful for the treatment of oedematous syndromes, treatment of cardiac insufficiencies, certain obesities, cirrhosis, treatment of servere and refractory edemas, congestive cardiac insufficiency and for prolonged treatment of arterial hypertension.

The novel method of the invention for relieving pain in warm-blooded animals, including humans, comprises administering to warm-blooded animals an analgesically effective amount of at least one compound of formula I, its acid addition salts and its hydrates. The compounds may be administered orally, rectally, parenterally or topically to the skin and mucous. The usual daily dose is 0,66 to 13,33 mg/kg depending on the condition being treated, the specific compound and the method of administration. The method may also be used to treat ventricular, supraventricular and junctional arythmia at a dose of 3 to 12 mg/kg.

The starting compounds of formula II wherein $R_1$ and $R_2$ are hydrogen, halogen or alkyl of 1 to 5 carbon atoms may be prepared by oxidation of the corresponding indane. The other compounds of formula II, especially those wherein $R_1$ and $R_2$ are tetrahydrofuran, may be prepared by the following reaction scheme

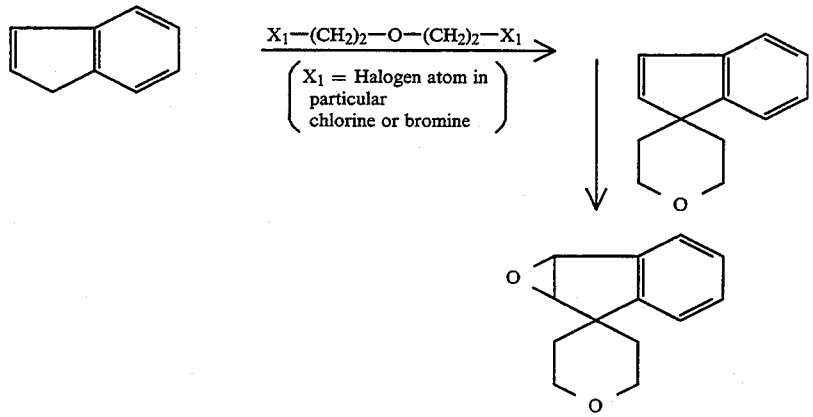

The novel intermediates of the invention are those of formulae IV, VI, VII, IX and XI wherein $R_6$ and $R_7$ are not both hydrogen.

In the following examples there are described several preferred embodiments to illustrate the invention. However, it is to be understood that the invention is not intended to be limited to the specific embodiments.

EXAMPLE 1

(1S,2S)
N-[2,3-dihydro-2-(1-pyrrolidinyl)-1H-inden-1-yl]-N-methyl-3-nitro-benzeneacetamide and its hydrochloride hydrated or anhydrous A mixture of 381 mg of 3-nitro-phenyl-acetic acid, 341 mg of carbonyldiimidazole and 3 ml of tetrahydrofuran was stirred for one hour at room temperature and then 350 mg of isomer B of trans 2,3-dihydro-N-methyl-2-(1-pyrrolidinyl)-1H-inden-1-amine with a specific rotation of $[\alpha]_D = +10.5°$ (c=1% in methanol) [prepared in Example 16A of EP 0,258,096] were added all at once. The mixture was rinsed with 3 ml of tetrahydrofuran and the suspension was stirred for 30 hours at room temperature. The mixture was distilled to dryness under reduced pressure and the residue was taken up in 30 ml of ethyl acetate and washed with 10 ml of a saturated sodium bicarbonate solution and then with water. The wash waters were extracted with ethyl acetate and the organic phase was dried, filtered, rinsed and evaporated to dryness to obtain 594 mg of residue. 564 mg of the residue were chromatographed over silica and eluted with ethyl acetate containing 2% of triethylamine to obtain 502 mg of purified expected free base.

470 mg of the purified base product were dissolved in 3 ml of ethyl acetate saturated with water and the solution was filtered and rinsed with 7 ml of ethyl acetate saturated with water. 0.3 ml of 6N hydrochloric acid in ethanol were added and the gum formed was concentrated and vacuum filtered to obtain white crystals which were rinsed with ethyl acetate, then ether and dried to obtain 447 g of the hydrated hydrochloride of the expected product melting at 140°–142° C. The product had a specific rotation of $[\alpha]_D = +74° \pm 1.5°$ (c=0.9% in H$_2$O).

| Circular dichroism in ethanol: | |
| --- | --- |
| Max. at 206 nm | $\Delta\epsilon = +19$ |
| Max. at 216 nm | $\Delta\epsilon = +17.4$ |
| Max. at 221 nm | $\Delta\epsilon = +15.5$ |
| Inflexion towards 320 mn | $\Delta\epsilon = +0.05$ |
| Max. at 265 nm | $\Delta\epsilon = +0.93$ |
| Max. at 272 nm | $\Delta\epsilon = +0.98$ |

3.24 g of isomer B of trans 2,3-dihydro-N-methyl-2-(1-pyrrolidinyl)-1H-inden-1-amine were reacted as described above to obtain 6.9 g of product which was dissolved at 20° C. in 20 ml of dimethoxyethane containing 2% water. 3.5 ml of an ethanolic solution of hydrogen chloride were added and crystallization in the cold was induced. The mixture was iced at 0° to 5° C. for 30 minutes and vacuum filtered at 0° C. The product was rinsed with dimethoxyethane and then ether and dried at 80° C. under reduced pressure to obtain 5.83 g of the desired hydrochloride melting at ≈220° C. The product was dissolved in 305 ml of dimethoxyethane containing 5% of water and the solution was filtered, rinsed and evaporated under reduced pressure to a volume of 70 ml to isolate in the same manner 5.66 g of non-solvated hydrochloride melting at 220°–222° C. and having a specific rotation of $[\alpha]_D = +70° \pm 2°$ (c=1% in H$_2$O).

EXAMPLE 2

(1R,2R)
N-[2,3-dihydro-2-(1-pyrrolidinyl)-1H-inden-1-yl]-N-methyl-3-nitro-benzene-acetamide and its sesquihydrated or anhydrous hydrochloride Using the procedure of Example 1, 1.045 g of isomer A of trans 2,3-dihydro-N-methyl-2-(1-pyrrolidinyl)-1H-inden-1-amine with a specific rotation of $[\alpha]_D = 10.5°$ (c=1% in methanol) prepared as described in Example 16A of EP application 0,258,096 were reacted to obtain 1.77 g of the purified free base product.

1.688 g of the said product were reacted with hydrogen chloride to obtain 1.699 g of the hydrochloride sesquihydrate with a specific rotation of $[\alpha]_D = -71.5° \pm 1.5°$ (c=1% in H$_2$O).

| Circular dichroism in ethanol: | |
| --- | --- |
| Max. at 210 nm | $\Delta\epsilon = -16.9$ |
| Max. at 215 nm | $\Delta\epsilon = -17$ |
| Max. at 221 nm | $\Delta\epsilon = -15.6$ |
| Inflexion towards 323 nm | $\Delta\epsilon = -0.08$ |
| Max. at 266 nm | $\Delta\epsilon = -1$ |
| Max. at 272 nm | $\Delta\epsilon = -1$ |

Using the procedure of Example 1, 0.43 g of the A isomer of Example 16A of European application No. 0,258,096 was reacted to obtain 661 mg of the anhydrous hydrochloride. The latter was dissolved in 27 ml of dimethoxyethane containing 5% of water and the solution was concentrated to a reduced volume to obtain 432 mg of the anhydrous hydrochloride melting at 220° to 222° C. and having a specific rotation of $[\alpha]_D = -76° \pm 1.5°$ (c=1% in H$_2$O).

EXAMPLE 3

Trans (±)
3,5-bis-(1,1-dimethylethyl)-N-[2,3-dihydro-2-(1-pyrrolidinyl)-1H-inden-1-yl]-4-hydroxy-N-methyl-benzamide and its hydrochloride A mixture of 7 g of 3,5-ditert.-butyl-4-hydroxy-benzoic acid and 7 ml of thionyl chloride was stirred under an inert atmosphere at room temperature for one hour, then stirred at 60° C. for 15 minutes and evaporated to dryness under reduced pressure. The crystalline residue was empasted in pentane, vacuum filtered and the filtrate was evaporated to dryness to obtain 7 g of the acid chloride. A mixture of 3 g of trans (±) 2,3-dihydro-N-methyl-2-(1-pyrrolidinyl)-1H-inden-1-amine in 30 ml of methylene chloride and 1.93 ml of triethylamine was cooled to 0° C. and 4.2 g of the acid chloride were slowly added thereto. The temperature was allowed to return to room temperature and the mixture was stirred for 4 hours and evaporated to dryness under reduced pressure. The residue was diluted with water and was extracted with ethyl acetate. The organic phase was washed with water, dried and evaporated to dryness to obtain 6 g of raw product. The latter was chromatographed over silica and eluted with a 9-1 ethyl acetate-triethylamine mixture to obtain 4 g of the free base product.

The base was dissolved in 40 ml of ethyl acetate and an ethanol solution saturated with hydrogen chloride was added. The mixture was iced and vacuum filtered and the product was dried at 80° C. under reduced pressure to obtain 3.4 g of the corresponding hydrochloride melting at >260° C. after crystallization from isopropanol.

EXAMPLE 4

Trans (±) N-[5-chloro-(2,3-dihydro-2-(1-pyrrolidinyl)-1H-inden-1-yl]-N-methyl-3-nitro-benzene-acetamide and its hydrochloride A mixture of 912 mg of m-nitro-phenyl-acetic acid, 813 mg of carbonyldiimidazole and 10 ml of tetrahydrofuran was stirred at room temperature for one hour 1,7 cm3 of triethylamine is added and then 1.55 g of the oxalate of trans (±) 5-chloro-2,3-dihydro-N-methyl-2-(1-pyrrolidinyl)-1H-inden-1-amine were added. The mixture was stirred for 6 hours and was evaporated to dryness under reduced pressure. The residue was taken up in 30 ml of ethyl acetate and the solution was washed with an aqueous 10% sodium bicarbonate solution, dried and evaporated to dryness to obtain 1.73 g of the desired base compound.

1.45 g of the base were dissolved in 10 ml of isopropanol at 20° C. and 1 ml of ethanolic hydrogen chloride was added. The mixture was partially concentrated under reduced pressure and the crystalline product was trituated in 10 ml of isopropanol and vacuum filtered. The product was rinsed with isopropanol and then with ether and dried at 60° C. to obtain 1.19 g of the hydrochloride which melted at 223° to 225° C. after crystallization from ethanol.

| Analysis: | | | | | | | | |
|---|---|---|---|---|---|---|---|---|
| Calculated: | % C | 58.67 | % H | 5.59 | % N | 9.33 | % Cl | 15.74 |
| Found: | | 58.6 | | 5.6 | | 9.3 | | 15.7 |

EXAMPLE 5

1S, trans N-(5-chloro-[2,3-dihydro-2-(1-pyrrolidinyl)-1H-inden-1-yl]-N-methyl-3-nitro-benzene-acetamide and its methanesulfonate STEP A: Isomer A of trans (−) 5-chloro-2,3-dihydro-1-(1-pyrrolidinyl)-1H-inden-1-amine 50 ml of ether were added at 20° C. to a solution of 6.83 g of the oxalate of trans (±) 5-chloro-2,3-dihydro-1-(1-pyrrolidinyl)-1H-inden-1-amine prepared by Example 31 of European patent application No. 0,258,096 in 10 ml of water and then 10 ml of potassium hydroxide solution were slowly added with stirring. The decanted aqueous phase was extracted with ethyl acetate and the organic phase was dried and evaporated to dryness under reduced pressure to obtain 4.25 g of the desired base.

A solution of 4.19 g of the base in 20 ml of methanol was admixed with a solution of 6.62 g of L(−) di-p-tolyl-tartaric acid in 60 ml of methanol and crystallization was induced. The mixture was held at 20° C. for 16 hours, iced for one hour and was vacuum filtered. The crystals were washed with methanol and then with ether and crystallized from methanol to obtain 2.8 g of the salt of isomer A melting at ≈180° C. and having a specific rotation of $[\alpha]_D = -33° \pm 1.5°$ (c=1% in dimethylformamide).

3 ml of potassium hydroxide solution were added to a solution of 2.75 g of the salt of isomer A, 10 ml of water and 50 ml of ether and was filtered. The filtrate was extract with ether and the organic phase was dried and concentrated to dryness under reduced pressure to obtain 1.077 g of the desired product with a specific rotation of $[\alpha]_D = -9° \pm 2°$ (c=0.5% in methanol).

STEP B: 1S trans N-(5-chloro-[2,3-dihydro-2-(1-pyrrolidinyl)-1H-inden-1-yl]-N-methyl-3-nitro-benzene-acetamide and its methane sulfonate Using the procedure of Example 1, 904 mg of m-nitro-phenyl-acetic acid, 964 mg of isomer A of Step A, 809 mg of carbonyldiimidazole and 13 ml of tetrahydrofuran were reacted to obtain 1.59 g of raw product. The latter was dissolved in 10 ml of ethanol and 0.3 ml of methane sulfonic acid was added. Crystallization was effected at 20° C. and the mixture was vacuum filtered. The product was rinsed with ethanol, then with ether and dried at 60° C. under reduced pressure to obtain 1.30 g of the methane sulfonate which melted at 215° to 216° C. after crystallization from ethanol and had a specific rotation of $[\alpha]_D = +82° \pm 2°$ (c=1% in H₂O).

| Circular dichroism in ethanol: | |
|---|---|
| Max. at 227 nm | Δε = 19.5 |
| Inflexion towards 295 nm | Δε = 0.2 |

EXAMPLE 6

1R, trans N-(5-chloro-[2,3-dihydro-2-(1-pyrrolidinyl)-1H-inden-1-yl]-N-methyl-3-nitro-benzene-acetamide and its methane sulfonate STEP A: Isomer B of trans (±) 5-chloro-2,3-dihydro-1-(1-pyrrolidinyl)-1H-inden-1-amine The methanolic mother liquors of Step A of Example 5 obtained by filtration of the salt of isomer A were evaporated to dryness and the residue was taken up in water, ether and potassium hydroxide as in Example 5 to obtain 3.2 g of the free base which was dissolved in a solution of 80 ml of methanol and 4.75 g of D (+) p-tolyl-tartaric acid monohydrate. Crystallization was induced and after standing for 3½ hours at 20° C., the mixture was vacuum filtered to obtain 3.28 g of the salt of isomer B of the desired product melting at ≈180° C. after crystallization from methanol. The product had a specific rotation of $[\alpha]_D = +32° \pm 1.5°$ (c=1% in dimethylformamide)

3.21 g of the salt were reacted as in Step A of Example 5 to obtain 1.267 g of the desired product with a specific rotation $[\alpha]_D = +8.5° \pm 2°$ (c=0.5% in methanol).

STEP B: 1R, trans N-(5-chloro-[2,3-dihydro-2-(1-pyrrolidinyl)-1H-inden-1-yl]-N-methyl-3-nitro-benzene-acetamide and its methanesulfonate Using the procedure of Step B of Example 5, 501 mg of the B isomer of the amine were reacted to obtain 859 mg of the free base and then 694 mg of the methanesulfonate of it melting at 215° to 216° C. It had a specific rotation of $[\alpha]_D = -87.5° \pm 2°$ (c=1% in H₂O).

| Circular dichroism in ethanol: | |
|---|---|
| Max. at 226 nm | Δε = −20 |

| Circular dichroism in ethanol: | | Analysis: $C_{22}H_{22}Cl_2N_2O.HCl$ | | | | | | | |
|---|---|---|---|---|---|---|---|---|---|
| Inflexion towards 290 nm | $\Delta\epsilon = -0.2$ | Calculated: | % C | 60.36 | % H | 5.29 | % N | 6.40 | % Cl | 24.29 |
| | | Found: | | 60.3 | | 5.2 | | 6.3 | | 24.0 |

EXAMPLE 7

Trans (±)
N-[3,4-dichloro-N-(2,3-dihydro-2-(2,5-dihydro-1H-pyrrol-1-yl))-1H-inden-1-yl]-N-methyl-benzene-acetamide and its hydrochloride

STEP A: Trans (±) 2,3-dihydro-1-(2,5-dihydro-1H-pyrrol-1-yl)-1H-inden-2-ol

A solution of 10 g of 2,5-dihydro-1H-pyrrole (2-butenedioate) and 6 g of sodium carbonate in 20 ml of water was added at 20° C. to a solution of 7.4 g of 1a,6a-dihydro-6H-indeno [1,2-b] oxirene in 5 ml of water and the mixture was heated at 70° C. for 4 hours and allowed to cool to room temperature. 15 ml of sodium hydroxide solution were added and the mixture was extracted with ethyl acetate. The organic phase was dried and evaporated to dryness under reduced pressure to obtain 8.62 g of raw product. The latter was chromatographed over silica and eluted with a 98-2 ethyl acetate-triethylamine mixtures to obtain the desired product.

STEP B: Dinitrate of trans (±) 2,3-dihydro-2-(2,5-dihydro-1H-pyrrol-1-yl)-N-methyl-1H-inden-1-amine A solution of 1.4 ml of methanesulfonyl chloride in 2 ml of tetrahydrofuran was added over 5 minutes at −20° C. to a mixture of 3.03 g of the product of Step A, 2.7 ml of triethylamine and 25 ml of tetrahydrofuran formed at 20° C. and after stirring for 15 minutes, the temperature was allowed to rise to 0° C. 20 ml of a 33% ethanol solution of methylamine were added to the mixture was stirred while the temperature returned to room temperature. The tetrahydrofuran was distilled under reduced pressure and the residue was taken up in 30 ml of ethyl acetate. 40 ml of sodium hydroxide solution were added and the mixture was diluted in half with stirring. The decanted aqueous phase was extracted with ethyl acetate. The organic phase was evaporated to dryness and the 3.27 g of residue were dissolved in 10 ml of ethyl acetate. A solution of 1.4 ml of fuming nitric acid in 10 ml of ethyl acetate was added thereto at 10° C. and the mixture was decanted. The residue was taken up in 10 ml of ethanol and the solution was refluxed. Crystallization was induced and the mixture was vacuum filtered. The product was dried at 20° C. under reduced pressure to obtain 3.83 g of the desired product which melted at 172° to 173° C. after crystallization from ethanol.

STEP C: Trans (±) 3,4-dichloro-N-[2,3-dihydro-2-(2,5-dihydro-1H-pyrrol-1-yl)-1H-inden-1-yl]-N-methyl-benzene-acetamide and its hydrochloride Using the procedure of Example 4, 533 mg of 3,4-dichlorophenyl-acetic acid and 680 mg of the product of B were reacted to obtain 954 mg of the free base and then 530 mg of the hydrochloride melting at 237° to 239° C.

EXAMPLE 8

Trans (±)
N-[5,6-dichloro-2,3-dihydro-2-(1-pyrrolidinyl)-1H-inden-1-yl]-N-methyl-3-nitro-benzene-acetamide and its hydrochloride

STEP A: 5,6-dichloro-2,3-dihydro-1H-inden-1-one

A mixture of 20 g of 3-(3,4-dichlorophenyl)-propionic acid [J. Med. Chem., Vol. 16(2) (1973), p. 101–106] and 100 ml of thionyl chloride was refluxed for 30 minutes and the thionyl chloride was then evaporated. The residue was taken up in 20 ml of methylene chloride and the solution was poured into a suspension of 20 g of aluminum chloride in 150 ml of methylene chloride. The mixture was stirred for one hour at room temperature and 30 minutes at 50° C. The mixture was poured over ice and was stirred for 30 minutes and then was extracted with methylene chloride. The organic phase was washed with water, dried and evaporated to dryness and the residue was taken up in ether and vacuum filtered. The product was dried to obtain 80 g of the desired product melting at 155° C.

STEP B: 5,6-dichloro-2,3-dihydro-1H-inden-1-ol 4.85 g of sodium borohydride were added at 0° C. to a solution of 4 g of the product of Step A in 285 ml of methanol and after stirring for one hour, the methanol was evaporated. The residue was diluted with water and excess hydride was eliminated by addition of hydrochloric acid. The mixture was extracted with ethyl acetate and the organic phase was evaporated to dryness under reduced pressure to obtain the desired product melting at 84° C.

STEP C: 5,6-dichloro-1H-indene

A mixture of 17.48 g of the product of Step B, 470 ml of toluene, 0.57 g of 4-tert.-butyl-catechol and 1.63 g of p-toluene sulfonic acid was refluxed for 2 hours and then was diluted with water. 10 ml of N sodium hydroxide solution were added and the mixture was extracted with toluene. The organic phase was evaporated to dryness under reduced pressure and the residue was taken up in hexane. The mixture was vacuum filtered and the crystalline product was dried to obtain 9 g of the desired product melting at 76° C.

STEP D: Trans (±) 4,5-dichloro-1aH-indeno[1,2-b]oxirene

A mixture of 8 g of the product of Step C, 56 ml of methylene chloride, 140 ml of an aqueous 10% sodium bicarbonate solution and 12 g of sodium bicarbonate was cooled to −7° C. and 15.6 g of m-chloropenbenzoic acid were added while keeping the temperature below 10° C. The mixture was stirred for 16 hours at room temperature and after the addition of 0.7 g of sodium hyposulfite, the mixture was extracted with methylene chloride. The combined organic phases were washed with water, dried and evaporated to dryness under reduced pressure to obtain 9.2 g of the desired product which was used as is for the next step.

STEP E: Trans (±) 5,6-dichloro-2,3-dihydro-1-(1-pyrrolidinyl)-1H-inden-2-ol

A mixture of 10 ml of pyrrolidine and 10 ml of water was added over 20 minutes to 12 g of the product of Step D and the mixture was heated at 60° C. for one hour and then cooled. An aqueous saturated sodium chloride solution was added to the mixture which was extracted with ether. The organic phase was dried and evaporated to dryness under reduced pressure to obtain 14 g of raw product. The latter was chromatographed over silica and eluted with a 97-3 ethyl acetate-triethylamine mixture to obtain the desired product melting at 120° C.

STEP F: Trans (±) 5,6-dichloro-2,3-dihydro-N-methyl-2-(1-pyrrolidinyl)-1H-inden-1-amine A solution of 17 ml of methane sulfonyl chloride in 3 ml of tetrahydrofuran was added dropwise at −20° C. to a mixture of 5 g of the product of Step E, 40 ml of tetrahydrofuran and 4 ml of triethylamine and after stirring for 15 minutes at −20° C., the temperature was raised to 0° C. and 20 ml of methylamine in ethanol were added. The mixture was stirred for 22 hours and was evaporated to dryness. The residue was diluted with water and after the addition of a few drops of sodium hydroxide solution, the mixture was extracted with ethyl acetate. The organic phase was washed with aqueous sodium chloride solution, dried and evaporated to dryness under reduced pressure to obtain 5.7 g of residue. The latter was chromatographed on silica and eluted with a 8-1-1 ethyl acetate-methanol-triethylamine mixture and after standing at 4° C., 4.91 g of the desired crystalline product melting at ≈55° C. were obtained.

STEP G: Trans (±) N-(5,6-dichloro-2,3-dihydro-2-(1-pyrrolidinyl)-1H-inden-1-yl]-N-methyl-3-nitro-benzene-acetamide and its hydrochloride Using the procedure of Example 1, 579 mg of 3-nitrophenylacetic acid, 518 mg of carbonyldiimidazole, 5 ml of tetrahydrofuran, 800 ml of the product of Step F and 2 ml of tetrahydrofuran were reacted to obtain 1 g of the desired free base and then 1 g of the raw hydrochloride which was crystallized from a methanol-isopropanol mixture and then ethanol to obtain 563 mg of pure hydrochloride melting at 185° to 190° C.

Analysis: $C_{22}H_{24}Cl_3N_3O_3$

| | % C | % H | % N | % Cl |
|---|---|---|---|---|
| Calculated: | 54.5 | 4.99 | 8.67 | 21.94 |
| Found: | 54.4 | 5.0 | 8.6 | 21.8 |

EXAMPLE 9

Trans (±) 3,4-dichloro-N-[2,3-dihydro-2-[methyl-(2-phenethyl)-amino]-1H-inden-1-yl]-N-methyl-benzene-acetamide and its hydrochloride

STEP A: Trans (±) 2,3-dihydro-1-[methyl-(2-phenethyl)-amino]-1H-inden-2-ol-N-methyl-benzene-acetamide and its hydrochloride 6.5 g of N-methyl-phenylethylamine were added to a mixture of 5.68 g of 1a,6a-dihydro-6H-indeno[1,2-b]oxirene in 15 ml of water and after heating at 50° to 55° C. for one hour, the mixture returned to 20° C. and was saturated with sodium chloride. 1 ml of sodium hydroxide solution was added and the mixture was extracted with ethyl acetate. The organic phase was washed with aqueous sodium chloride solution, dried and evaporated to dryness under reduced pressure to obtain 13.21 g of the desired free base. The latter was dissolved in 45 ml of ether and 15 ml of a 6.6N hydrogen chloride in ethanol solution were added. Crystallization was induced and after standing at room temperature for one hour, the mixture was vacuum filtered. The product was dried at 80° C. under reduced pressure to obtain 8.87 g of the hydrochloride melting at 158° to 162° C.

STEP B: Trans (±) 2,3-dihydro-N-methyl-2-[methyl-(2-phenethyl)-1H-inden-1-amine and its dihydrochloride Using the procedure of Step B of Example 7, 8.38 g of the hydrochloride of Step A were reacted to obtain 8.44 g of the desired free base. 8.36 g of the base were dissolved in 30 ml of ether and 20 ml of ethanol and after the addition of 10 ml of ethanolic hydrogen chloride solution, crystallization was induced. The mixture stood at 20° C. and was then vacuum filtered. The product was rinsed with a 1-1 ethanol-ether mixture, then with ether and dried at 80° C. under reduced pressure to obtain 7.6 g of the desired dihydrochloride which melted at 234° to 237° C. (decomposition) after crystallization from isopropanol.

Analysis:

| | % C | % H | % N | % Cl |
|---|---|---|---|---|
| Calculated: | 64.59 | 7.42 | 7.93 | 20.07 |
| Found: | 64.4 | 7.4 | 7.9 | 20.0 |

STEP C: Trans (±) 3,4-dichloro-N-[2,3-dihydro-2-[methyl-(2-phenethylamino]-1H-inden-1-yl]-N-methyl-benzene-acetamide and its hydrochloride Using the procedure of Example 4, 800 mg of 3,4-dichlorophenylacetic acid, 632 mg of carbonyldiimidazole in 8 ml of tetrahydrofuran, 0.84 ml of triethylamine and 1.060 g of the dihydrochloride of Step B were reacted to obtain 1.625 g of the desired free base. 1.424 g of the said product were reacted with 0.6 ml of a 6.6N hydrogen chloride in ethanol solution to obtain 1.0 g of the desired hydrochloride melting at 200° to 202° C.

Analysis: $C_{27}H_{28}Cl_2N_2O\cdot HCl$

| | % C | % H | % N | % Cl |
|---|---|---|---|---|
| Calculated: | 64.36 | 5.80 | 5.56 | 21.11 |
| Found: | 64.2 | 5.6 | 5.5 | 21.2 |

EXAMPLE 10

Trans (±)
3,4-dichloro-N-[2,3-dihydro-2-[2-(furymethyl)-methylamino]-1H-inden-1-yl]-N-methyl-benzene-acetamide

STEP A: Trans (±) 2,3-dihydro-1-[2-(furylmethyl)-methylamino]-1H-inden-2-ol and its hydrochloride Using the procedure of Step A of Example 9, 7 g of 1a,6a-dihydro-6H-indeno[1,2-b]oxirene, 5.26 g of (furylmethyl)-methylamine and 10 ml of water were reacted to obtain 9.86 g of the desired free base which was chromatographed over silica. Elution with a 4–6 ethyl acetate-methylene chloride mixture yielded 406 mg of an oil which was added to 20 ml of ethyl acetate and 0.5 ml of a 6.6N hydrogen chloride in ethanol solution to obtain 412 mg of the hydrochloride melting at 145° to 148° C.

Analysis: $C_{15}H_{18}O_2NCl$

| | % C | % H | % N | % Cl |
|---|---|---|---|---|
| Calculated: | 64.40 | 6.48 | 5.00 | 12.67 |
| Found: | 64.4 | 6.7 | 4.9 | 12.7 |

STEP B: Trans (±) 2,3-dihydro-N-[methyl-(2-furylmethylamino]-1H-indene-1-amine hydrochloride Using the procedure of Step B of Example 7, 5.83 g of the base of Step A were reacted to obtain 3.69 g of the desired hydrochloride melting at 180° to 184° C. (decomposition) after crystallization from ethanol.

STEP C: Trans (±) 3,4-dichloro-N-[2,3-dihydro-2-[2-(furyl-methyl)-methylamino]-1H-inden-1-yl]-N-methyl-benzene-acetamide and its butenedioate Using the procedure of Example 4, 800 mg of 3,4-dichlorophenyl-acetic acid, 632 mg of carbonyl-diimidazole in 8 ml of tetrahydrofuran, 0.6 ml of triethylamine and 1.14 g of the hydrochloride of Step B were reacted to obtain 1.606 g of the desired base. 1.490 g of the base were dissolved in 10 ml of ethyl acetate and 348 mg of maleic acid were added at 20° C. The mixture was heated for total dissolution and crystallization was induced in the cold. The mixture was cooled and vacuum filtered. The product was rinsed with ethyl acetate, then with ether and dried at 20° C. under reduced pressure to obtain 1,55 g of the desired product melting at 154° to 156° C. after crystallization from ethanol.

Analysis: $C_{24}H_{24}Cl_2N_2O$; molecular weight = 559.45

| | % C | % H | % N | % Cl |
|---|---|---|---|---|
| Calculated: | 60.11 | 5.04 | 5.01 | 12.67 |
| Found: | 60.1 | 4.9 | 4.7 | 12.7 |

EXAMPLE 11

Trans (±)
3,4-dichloro-N-[2,3-dihydro-2-[4-(2-methoxyphenyl)-1-piperazinyl]-1H-inden-1-yl]-N-methyl-benzene-acetamide and it hydrochloride

STEP A: Trans (±) 2,3-dihydro-1-[2-(4-[2-methoxyphenyl-1-piperazinyl]-1H-inden-2-ol Using the procedure of Example 9, 5.68 g of 1a,6a-dihydro-6H-indeno[1,2-b]oxirene, 10 ml of water and 10 g of 1-(2'-methoxyphenyl)-piperazine were reacted to obtain 17.76 g of the desired free base which was chromatographed on silica. Elution with ethyl acetate yielded 655 mg of purified hydrochloride which was crystallized from ethanol to obtain 370 mg of hydrochloride melting at 152° to 154° C.

STEP B: Trans (±) 2,3-dihydro-N-methyl-2-[4-(2-methoxyphenyl)-1-piperazinyl]-1H-indene-1-amine hydrochloride Using the procedure of Step B of Example 7, 9.58 g of the base of Step A were reacted to directly obtain 3.49 g of the hydrochloride. The mother liquors were extracted with ethyl acetate and chromatographed on silica. Elution with a 85-10-5 ethyl acetate-methanol-triethylamine mixture yielded 5.81 g of the free base which was converted into the hydrochloride melting at 246° to 250° C.

STEP C: Trans (±) 3,4-dichloro-N-[2,3-dihydro-2-[4-(2-methoxyphenyl)-1-piperazinyl]-1H-inden-1-yl]-N-methyl-benzene-acetamide and its hydrochloride Using the procedure of Example 4, 800 mg of 3,4-dichlorophenyl-acetic acid, 632 mg of carbonyl-diimidazole in 8 ml of tetrahydrofuran, 1.01 g of the hydrochloride of Step B and 0.5 ml of triethylamine were reacted to obtain 1.94 g of the desired product 1,92 g of which was reacted to form the hydrochloride which was crystallized from isopropanol to obtain 1.08 g of hydrochloride melting at 217° to 220° C.

Analysis: $C_{29}H_{31}Cl_2N_3O_2$

| | % C | % H | % N | % Cl |
|---|---|---|---|---|
| Calculated: | 63.09 | 5.75 | 7.49 | 18.96 |
| Found: | 62.1 | 5.9 | 7.2 | 19.1 |

EXAMPLE 12

Tablets were prepared with 200 mg of the product of Example 1 and sufficient excipient of lactose, talc, starch and magnesium stearate for a final weight of 800 mg.

EXAMPLE 13

An intramuscular injectable solution was prepared with 50 mg of the product of Example 1 with sterile solvent for a final volume of 5 ml.

PHARMACOLOGICAL DATA

A. Diuretic Activity

Male rats of the Sprague Dawley strain weighing 180 to 200 g were held without food for 17 hours before the test but were given all the water they desired. Groups of 10 rats were used for each test dose and the rats received the test compound intraveinously in solution in physiological serum containing 0.9% of sodium chloride in a volume of 1 ml/kg. The urinary volume was measured one hour after the administration of the product and the urine was collected. The activity of the test product was expressed as a percentage of variation as compared to the urine volume of the controls. The results were:

| Compound | Dose in mg/kg | % variation in urine volume |
| --- | --- | --- |
| Product of Example 1 | 0.3 | +1530% |
|  | 1 | +3180% |
| Product of Example 9 of European application No. 0,258,096 | 0.3 | +850% |
|  | 1 | +1680% |

CONCLUSION

The percentage of increase in urine volume obtained with the compound of Example 1 at a dose of 0.3 mg/kg is comparable to that obtained with the compound of Example 9 of EPO application No. 0,258,096 at a dose of 1 mg/kg. The diuretic activity of the compound of Example 1 was not accompanied with a modification of electrolyte elimination and it is essentially an aqueous diuresis.

Various modifications of the compounds and method of the invention may be made without departing from the spirit or scope thereof and it is to be understood that the invention is intended to be limited only as defined in the appended claims.

What is claimed is:

1. A compound selected from the group consisting of (1S,2S)N-[2,3-dihydro-2-(1-pyrrolidinyl)-1H-inden-1-yl]-N-methyl-3-nitro-benzene-acetamide and its anhydrous hydrochloride, trans (±)N-[5,6-dichloro-2,3-dihydro-2-(1-pyrrolidinyl)-1H-inden-1-yl]-N-methyl-3-nitro-benzene-acetamide and its hydrochloride, 1S, trans N-[5-chloro-2,3-dihydro-2-(1-pyrrolidinyl)-1H-inden-1-yl]-N-methyl-3-nitro-benzene-acetamide and its methane-sulfonate, trans (±) N-[5-chloro-2,3-dihydro-2-(1-pyrrolidinyl)-1H-inden-1-yl]-N-methyl-3-nitro-benzene-acetamide and its hydrochloride, (1R, 2R) N-[3,3-dihydro-2-(1-pyrrolidinyl)-1H-inden-1-yl]-N-methyl-3-nitro-benzene-acetamide and its sequihydrate or anhydrous hydrochloride and 1R, trans N-[5-chloro-2,3-dihydro-2-(1-pyrrolidinyl)-1H-inden-1-yl]-N-methyl-3-nitro-benzene-acetamide and its methane sulfonate.

2. A diuretic composition comprising a diuretically effective amount of a compound of claim 1 and an excipient.

3. A method of inducing diuresis in warm-blooded animals comprising administering to warm-blooded animals a diuretically effective amount of a compound of claim 1.

* * * * *